United States Patent
Mazzoleni et al.

(10) Patent No.: US 11,602,669 B2
(45) Date of Patent: Mar. 14, 2023

(54) FITNESS TRACKING SYSTEM WITH VOICE INPUT

(71) Applicant: MYFITNESSPAL, INC., San Francisco, CA (US)

(72) Inventors: Michael Mazzoleni, Baltimore, MD (US); Jeffrey Allen, Baltimore, MD (US); Robert Lanzer, Baltimore, MD (US)

(73) Assignee: MyFitnessPal, Inc., San Francisco, CA (US)

(*) Notice: Subject to any disclaimer, the term of this patent is extended or adjusted under 35 U.S.C. 154(b) by 376 days.

(21) Appl. No.: 16/853,375

(22) Filed: Apr. 20, 2020

(65) Prior Publication Data

US 2021/0322826 A1 Oct. 21, 2021

(51) Int. Cl.
*A63B 24/00* (2006.01)
*A61B 5/00* (2006.01)
(Continued)

(52) U.S. Cl.
CPC ........ *A63B 24/0062* (2013.01); *A61B 5/6804* (2013.01); *A63B 23/1209* (2013.01);
(Continued)

(58) Field of Classification Search
CPC ............ A63B 24/0062; A63B 23/1209; A63B 23/1281; A63B 24/0075; A63B 2023/0411; A63B 2071/068; A63B 2220/17; A63B 2220/40; A63B 2220/50; A63B 2225/50; A61B 5/6804; A61B 5/6805; A61B 5/02416; A61B 5/0245; A61B 2562/0219; A61B 5/1118; G16H 20/30

See application file for complete search history.

(56) References Cited

U.S. PATENT DOCUMENTS

| | | | |
|---|---|---|---|
| 2017/0232294 A1* | 8/2017 | Kruger | A61B 5/7435 434/247 |
| 2019/0307983 A1* | 10/2019 | Goldman | A61B 5/165 |
| 2021/0153805 A1* | 5/2021 | Carpenter | A61B 5/681 |

OTHER PUBLICATIONS

Clark, Trever, "Finding and Logging Exercises: Cardio, Weights, Quick Find, Voice Log, Say, Quick Entry," https://help.carbmanager.com/en/articles/2645971-finding-and-logging-exercises-cardio-weights-quick-find-voice-log-say-quick-entry, available as of Nov. 2019.

* cited by examiner

*Primary Examiner* — Jeffrey S Vanderveen
(74) *Attorney, Agent, or Firm* — Maginot, Moore & Beck, LLP

(57) ABSTRACT

A method of operating a fitness tracking system including a plurality of sensors is disclosed herein. The method includes mounting a biometric monitoring device on an article of apparel worn by a user. The method further includes receiving a prompt indicating that the user intends to provide a verbal cue via a microphone provided on the biometric monitoring device. After receiving the verbal cue from the user one of a plurality of exercise modules is selected for execution by the processor. Each of the plurality of exercise modules is configured to generate workout metrics based at least in part on physiological data received from a first of the plurality of sensors without regard to physiological data from a second of the plurality of sensors. The selected exercise module generates workout metrics for the user for a limited period of time ranging from selection of the exercise module until occurrence of a termination event.

20 Claims, 6 Drawing Sheets

(51) Int. Cl.
*A63B 23/12* (2006.01)
*G16H 20/30* (2018.01)
*A63B 23/04* (2006.01)
*A63B 71/06* (2006.01)

(52) U.S. Cl.
CPC ...... *A63B 23/1281* (2013.01); *A63B 24/0075* (2013.01); *G16H 20/30* (2018.01); *A63B 2023/0411* (2013.01); *A63B 2071/068* (2013.01); *A63B 2220/17* (2013.01); *A63B 2220/40* (2013.01); *A63B 2220/50* (2013.01); *A63B 2225/50* (2013.01)

FITNESS TRACKING SYSTEM WITH VOICE INPUT

COPYRIGHT

A portion of the disclosure of this patent document contains material that is subject to copyright protection. The copyright owner has no objection to the facsimile reproduction by anyone of the patent document or the patent disclosure, as it appears in the United States Patent and Trademark Office patent files or records, but otherwise reserves all copyright rights whatsoever.

FIELD

The device and method disclosed herein relates to fitness tracking systems and, more particularly, to fitness tracking systems configured to monitor specific user activities.

BACKGROUND

Activity tracking devices and particularly wearable sensors are increasingly utilized by individuals interested in tracking metrics related to their personal health and fitness. One challenge with wearable sensors used to capture activity metrics relates to the great diversity and variability in human movement and physiology. There are two types of variability that pose a challenge: intra-individual variability and inter-individual variability. Intra-individual variability occurs when a single person performs many different types of exercises that all appear similar from the perspective of the sensor. For example, a sensor device may have difficulty determining whether the user performed a bench press, dumbbell curls, or squats. Inter-individual variability occurs when two individuals performing the same exercise generate data that has significant differences between the two individuals such that the sensor devices cannot determine that the individuals performed the same workout. For example, the sensor devices worn by two individuals performing the same dumbbell fly exercise may suggest that one individual performed the dumbbell fly exercise, but another performed lunges. Therefore, it would be advantageous to improve fitness tracking systems by providing one or more wearable sensors that are capable of accounting for both intra-individual variabilities and inter-individual variabilities. It would also be advantageous to provide a fitness tracking system and related method of operation such that the fitness tracking system is capable of accurately recognizing and tracking different exercises performed by users.

SUMMARY

In accordance with one exemplary embodiment of the disclosure, a fitness tracking system includes an article of apparel, a biometric monitoring device, and a plurality of sensors configured to be worn by a user and generate physiological data for the user. The article of apparel is configured to encircle a torso of a user and includes a receptacle. The biometric monitoring device is releasably mounted in the receptacle of the article of apparel. The biometric monitoring device includes a processor, a memory, a transceiver, at least one microphone, and at least one sensor of the plurality of sensors. The processor of the biometric monitoring device is configured to receive a prompt indicating that the user intends to provide a verbal cue via the at least one microphone, and then receive the verbal cue from the user via the at least one microphone. In response to the received verbal cue, the processor is configured to select one of a plurality of exercise modules for execution by the processor, each of the plurality of exercise modules configured to generate workout metrics based at least in part on physiological data received from a first sensor of the plurality of sensors without regard to physiological data from a second sensor of the plurality of sensors, each of the plurality of exercise modules associated with a termination event. The processor is further configured to execute the selected exercise module in order to generate workout metrics for the user, wherein execution of the selected exercise module occurs for a limited period of time ranging from selection of the exercise module until occurrence of the termination event.

In another embodiment of the disclosure, a method of operating a fitness tracking system is disclosed. The method includes receiving a prompt indicating that a user wearing a biometric monitoring device intends to provide a verbal cue via at least one microphone provided on the biometric monitoring device. The method further includes receiving the verbal cue from the user via the at least one microphone, and in response to the received verbal cue, selecting one of a plurality of exercise modules for execution by a processor of the biometric monitoring device, each of the plurality of exercise modules configured to generate workout metrics based at least in part on physiological data received from a first sensor worn by the user and without regard to a second sensor worn by the user, and each of the plurality of exercise modules associated with a termination event. Additionally, the method includes executing the selected exercise module in order to generate workout metrics for the user, receiving a termination event at the biometric monitoring device, and terminating execution of the selected exercise module following receipt of the termination event.

In yet another embodiment of the disclosure, a method of operating a fitness tracking system includes receiving, at a biometric monitoring device worn by a user, physiological data from a plurality of sensors worn by a user, each of the plurality of sensors positioned at a different location on a body of the user. The method further includes receiving a prompt indicating that the user intends to provide a verbal cue via at least one microphone provided on the biometric monitoring device, receiving the verbal cue from the user via the at least one microphone, and in response to the received verbal cue, selecting one of a plurality of exercise modules for execution by a processor of the biometric monitoring device. Additionally, the method includes generating workout metrics for the user using the selected exercise module, the generated workout metrics based at least in part on the physiological data received from one of a plurality of sensors worn by the user and without regard to physiological data received from another of the plurality of sensors worn by the user, and then transmitting the generated workout metrics to a personal electronic device.

These and other aspects of the disclosure shall become apparent when considered in light of the disclosure provided herein.

BRIEF DESCRIPTION OF THE DRAWINGS

The foregoing aspects and other features of a fitness tracking system are explained in the following description, taken in connection with the accompanying drawings.

All Figures © Under Armour, Inc. 2020. All rights reserved.

DETAILED DESCRIPTION

In the following detailed description, reference is made to the accompanying figures which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without parting from the spirit or scope of the present disclosure. It should be noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The terms "comprising," "including," "having," and the like, as used with respect to embodiments of the present disclosure, are synonymous.

Fitness Tracking System Including Biometric Monitoring Device with Microphone

Figure 1:
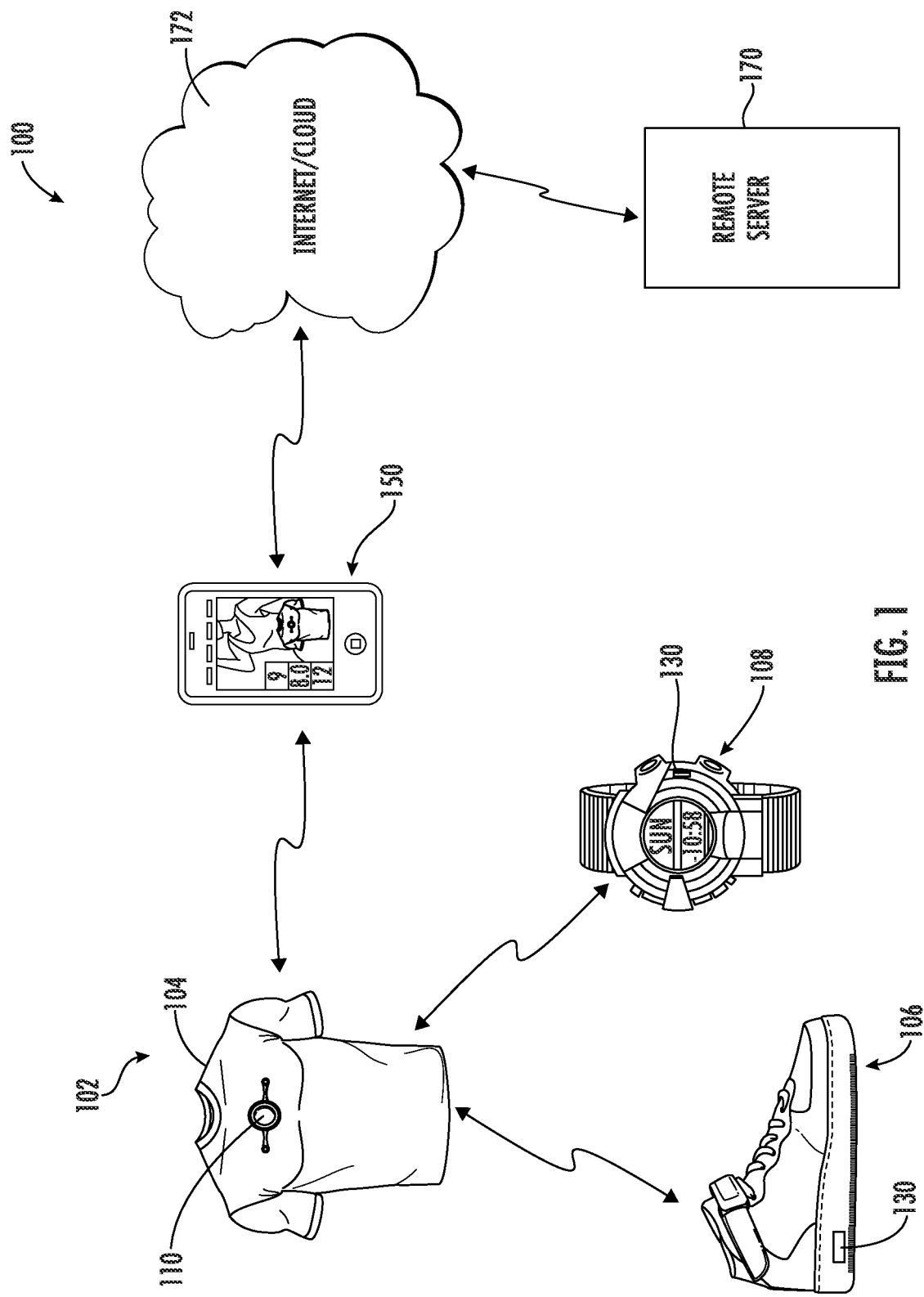
FIG. 1 is an illustration showing various components of a fitness tracking system.

With reference to FIG. 1, an exemplary embodiment of a fitness tracking system 100 is shown. The fitness tracking system 100 is configured to monitor and record fitness data for a user during an activity or workout. The fitness tracking system 100 (which may also be referred to herein as the "health tracking system" or the "activity tracking system") includes a voice activated biometric monitoring device 110 mounted on an article of apparel 102, such as a shirt 104 or chest strap. The biometric monitoring device 110 is in communication with one or more sensors 130 mounted on various additional articles of apparel worn by the user, such as a shoe 106 or a watch 108, or otherwise carried on the body of the user. The biometric monitoring device 110 is further configured for communication with a personal electronic device 150. The personal electronic device 150, in turn, is configured for communication with a remote server 170.

Figure 2:
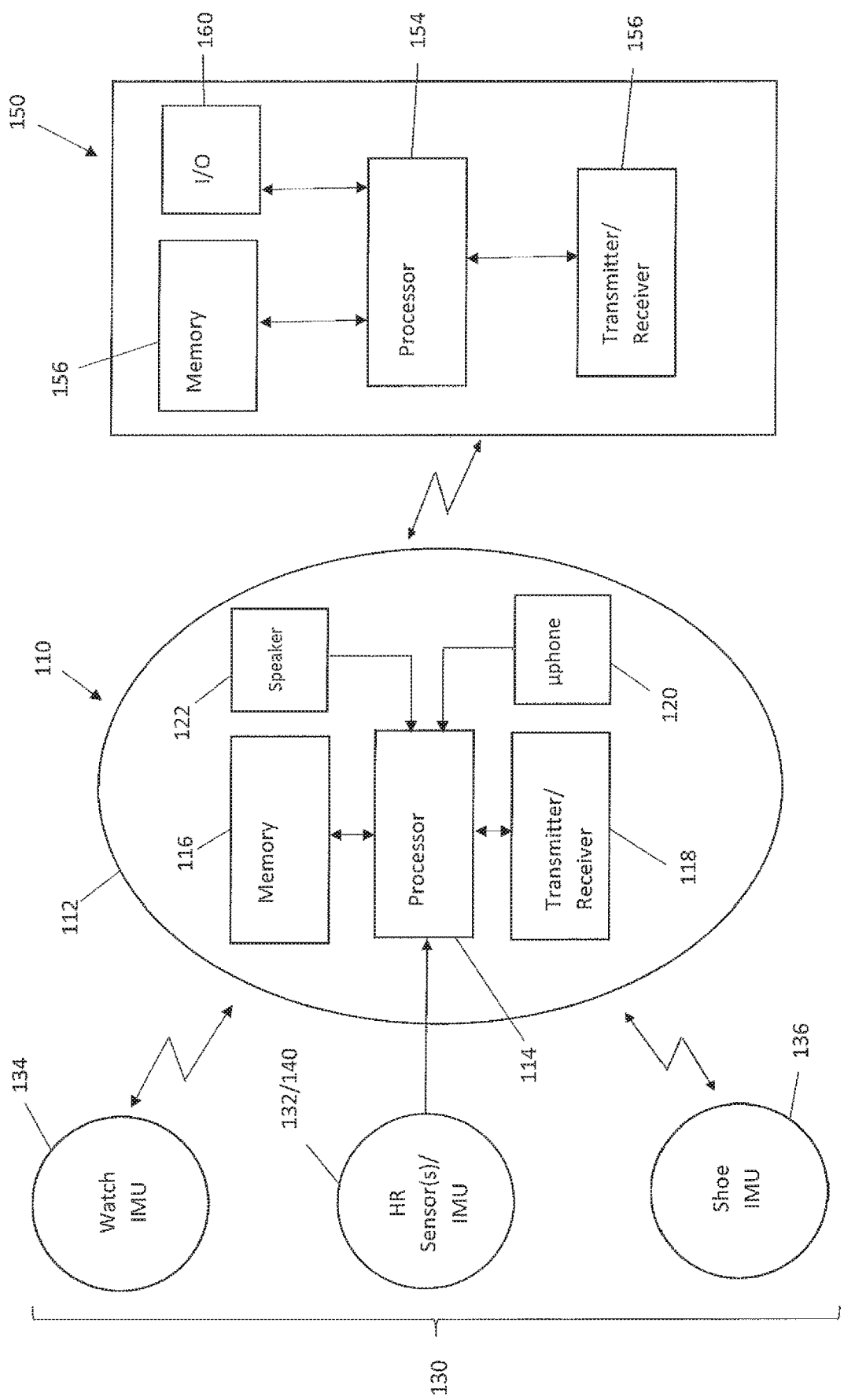
FIG. 2 is a block diagram of a biometric monitoring device in communication with a plurality of sensor components and a personal electronic device of the fitness tracking system of FIG. 1.

With reference to FIG. 2, the biometric monitoring device 110 includes a processor 114, a memory 116, a transceiver 118, a microphone 120, and a speaker 122, all encased within a housing 112. It will be recognized by those of ordinary skill in the art that a "processor" as used herein includes any hardware system, hardware mechanism or hardware component that processes data, signals, and/or other information. A processor can include a system with a central processing unit, multiple processing units, dedicated circuitry for achieving functionality, and/or other systems. The processor 114 is configured to receive data signals from the sensors 130, and/or other component parts of the biometric monitoring device 110 (such as the memory 116), and process such signals. The processor 114 is connected to the memory 116 and the transceiver 118, and may deliver processed data to one or both of the memory 116 and the transceiver 118. Additionally, the processor 114 may perform some processing on the received data prior to delivery thereof to the memory 116 or the transmitter/receiver 118. For example, the processor 114 may execute algorithms provided by the memory 116 in order to determine workout metrics related to the data provided by the sensors 130.

The memory 116 is configured to store information, including both data and instructions. The data may be delivered from the processor 114 and generally includes workout data, but may also include various types of operational data that may be ancillary to the basic operation of the biometric monitoring device 110. The instructions which are stored at the memory 116 generally include firmware and/or software for execution by the processor 114. Examples of such instructions include exercise modules that calculate different workout metrics within the fitness tracking app depending on an identified exercise, programs that control settings for the sensors 130, programs that control the receipt of information via the sensors 130, a program that controls the transmission and reception of data via the transmitter/receiver 118, as well as any of various other programs that may be associated with the biometric monitoring device 110. Such instructions may be present on the device 110 at the time of manufacture or may be downloaded thereto via well-known mechanisms.

The memory 116 may be of any type capable of storing information accessible by the processor 114, such as a memory card, ROM, RAM, write-capable, read-only memories, or other computer-readable medium. The data may be stored in the memory 116 in a relational database as a table having a plurality of different fields and records, XML documents, or flat files. The data may also be formatted in any computer-readable format such as, but not limited to, binary values, ASCII or Unicode.

In at least one embodiment, the memory 116 includes a fitness tracking application configured to execute a plurality of different sub-programs/subroutines, each related to a particular exercise routine being performed by the user. These sub-programs/subroutines are also referred to herein as "exercise modules." Examples of exercise modules stored in the memory 116 may include a first exercise module configured to determine workout metrics for a bench press routine, a second exercise module configured to determine workout metrics for a squat routine, and a third exercise module configured to determine workout metrics for a sit-up routine, etc. Further detail on the various exercise modules is provided in further detail below in the discussion associated with FIGS. 6 and 7. While the exercise modules are described herein as being stored in the memory 116 of the biometric monitoring device 110, in at least some alternative embodiments the exercise modules may alternatively be stored in different locations of the fitness tracking system, such as on a memory of the personal electronic device 150.

With continued reference to FIG. 2, the transceiver 118 is configured to allow the biometric monitoring device 110 to communicate with various other components of the fitness tracking system 100. For example, the transceiver 118 provides for wireless communication with the sensors 130 as well as the personal electronic device 150. In one embodiment, the transceiver 118 comprises an RF transmitter and receiver configured to transmit and receive communications signals over a network using a wireless communications technology, such as Wi-Fi or Bluetooth®, using any of various communications protocols, such as TCP/IP. Such transceivers are well known and will be recognized by those of ordinary skill in the art. The transceiver 118 is particularly configured to communicate with the personal electronic device 150 when the biometric monitoring device 110 is within a given short range of the personal electronic device 150, and transmit collected physiological data and/or workout metrics to the personal electronic device 150.

The microphone 120 of the biometric monitoring device 110 is configured to convert sound into electrical signals and deliver such signals to the processor 114. The microphone 120 is particularly configured to receive voice commands/instructions spoken by the user (e.g., "bench press 200 lbs." or "curl 30 lb. dumbbells") and deliver such voice commands to the processor. The microphone 120 may be any of various different types of microphones as will be recognized by those of ordinary skill in the art. For example, the microphone may be a dynamic microphone, a condenser microphone, or a piezoelectric microphone. Additionally, while only a single microphone is shown in the embodiment of FIG. 2, in at least some embodiments the biometric monitoring device 110 may include two or more microphones. Two or more microphones may be particularly advantageous for noise cancelling purposes. For example, a first microphone may be directed toward a user's head and a second microphone may be directed away from a user's head (e.g., a first microphone in the housing 112 that points upward, and a second microphone in the housing 112 that points downward or in a different direction). As a result, the two microphones of the biometric monitoring device 110 may be advantageously used for noise cancelling purposes.

The speaker 122 is configured to receive electrical audio signals from the processor 114 and convert such signals into sound. The speaker 122 is particularly configured to provide audio instructions to the user (e.g., "begin exercise" or "exercise complete"). The speaker 122 may be any of various different types of speakers as will be recognized by those of ordinary skill in the art. For example, the speaker may be a dynamic speaker or a piezoelectric speaker.

As noted previously, the various components of the biometric monitoring device 110, including the speaker 122, microphone 120, transceiver 118, memory 116 and processor 114 are all contained within a housing 112. The housing 112 is typically comprised of a relatively rigid and durable polymer material that protects the components contained therein. The housing 112 is designed and dimensioned such that the biometric monitoring device 110 may be easily grasped by a human and retained within a user's hand. For example, the dimensions of the housing 112 may be between one and two inches in height and width, and between ¼ and 1 inch in depth. The housing 112 may also include a power source, such as a battery (not shown) that powers all of the components within the housing 112. The battery may be a rechargeable or replaceable battery in order to allow for extended life of the biometric monitoring device.

The housing 112 encloses and retains numerous different components of the biometric monitoring device 110, including the battery, speaker 122, microphone 120, transceiver 118, memory 116 and processor 114. However, unlike the personal electronic device 150, the biometric monitoring device 110 does not include a graphical user interface or screen of any type. Thus, all user input and output from the device is via the microphone 120 and the speaker 122. Because the biometric monitoring device 110 is screen-less (i.e., is void of a screen providing a graphical user interface), it is more durable and resilient than other devices that include a screen. This also allows the biometric monitoring device to be advantageously positioned on the user in any of various locations, including unconventional locations removed from the user's line of sight.

Figure 3:
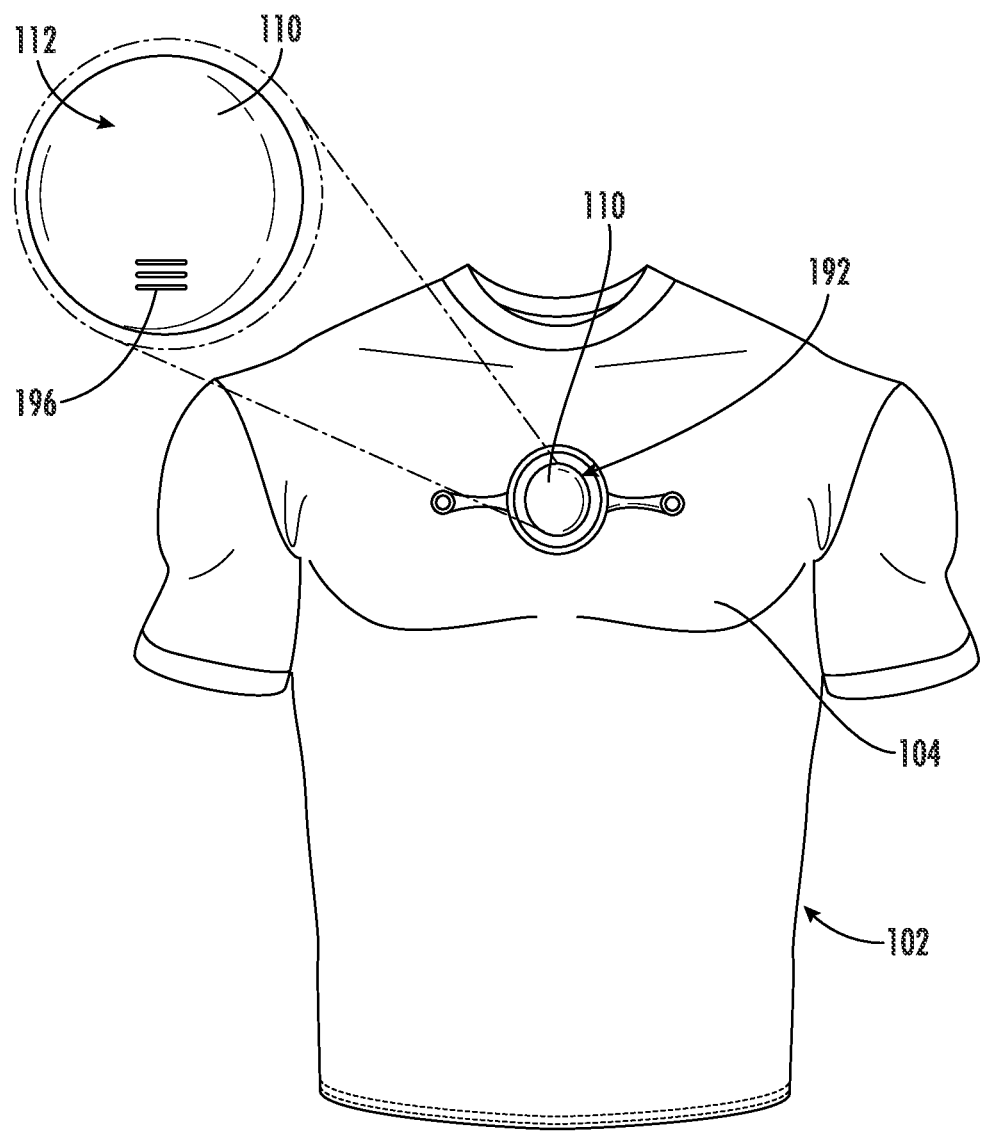
FIG. 3 is a front view of an article of apparel and the biometric monitoring device of FIG. 2.

With reference now to FIG. 3, in at least one embodiment, the various components of the biometric monitoring device 110 are provided within the housing 112, and the housing 112 is removably coupled to an article of apparel 102 worn by the user without destruction of either component. The article of apparel 102 may be provided in any of various forms including garments or accessories configured to be worn by the user. Examples of articles of apparel include shirts, pants, shorts, bras, chest straps, watches, hats, belts, watches, or any of various other articles of apparel. In at least one embodiment, the article of apparel is configured to encircle the torso of a wearer and substantially or at least partially cover the upper torso of the user (i.e., the torso above the waist). For example, the article of apparel 102 may be a shirt 104 (as shown in FIG. 3) configured to cover the entire upper torso of the user, a sports bra configured to cover a substantial portion of the upper torso of the user, or may be a chest strap that simply encircles the chest of the user but covers very little of the upper torso of the user.

With continued reference to FIG. 3, the article of apparel 102 includes a receptacle 192 designed to receive and retain the biometric monitoring device 110. The receptacle 192 may be provided in any of numerous forms, including the embodiments described in U.S. Pat. No. 10,021,188, issued Jun. 20, 2018, the contents of which are incorporated herein by reference in their entirety. The receptacle 192 is configured to mount or otherwise secure the biometric monitoring device 110 in place on the article of apparel 102 when it is worn by the user. In at least one embodiment, the receptacle 192 secures the biometric monitoring device 110 to the article of apparel 102 in a releasable fashion such that the biometric monitoring device 110 may be repeatedly released from and subsequently secured to the garment by the user without damaging the receptacle or the garment. To this end, the receptacle 192 may be comprised of a relatively strong but flexible polymer material. As a result, the biometric monitoring device 110 is securely retained within the receptacle 192 until a significant force is applied to the biometric monitoring device such that the receptacle is deformed and allows the biometric monitoring device 110 to be released. While the biometric monitoring device 110 has been described herein as being releasably mounted on the article of apparel via the receptacle 192, in an alternative embodiment, the biometric monitoring device 110 may be secured on the article of apparel 102 in a permanent fashion.

Figure 4:
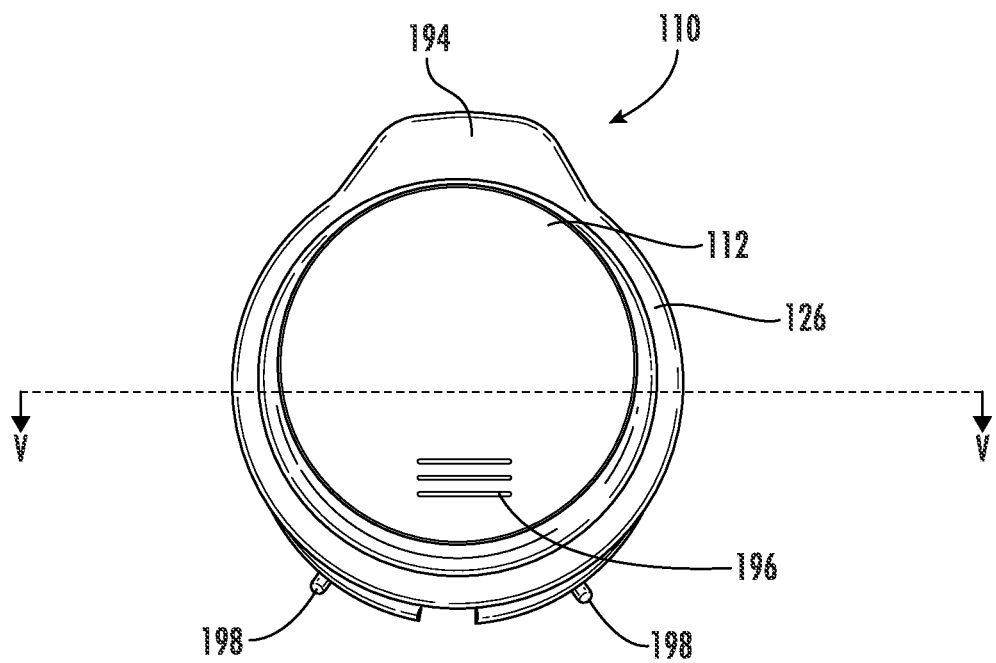
FIG. 4 is a front view of the biometric monitoring device of FIG. 3 in isolation from the article of apparel.
Figure 5:
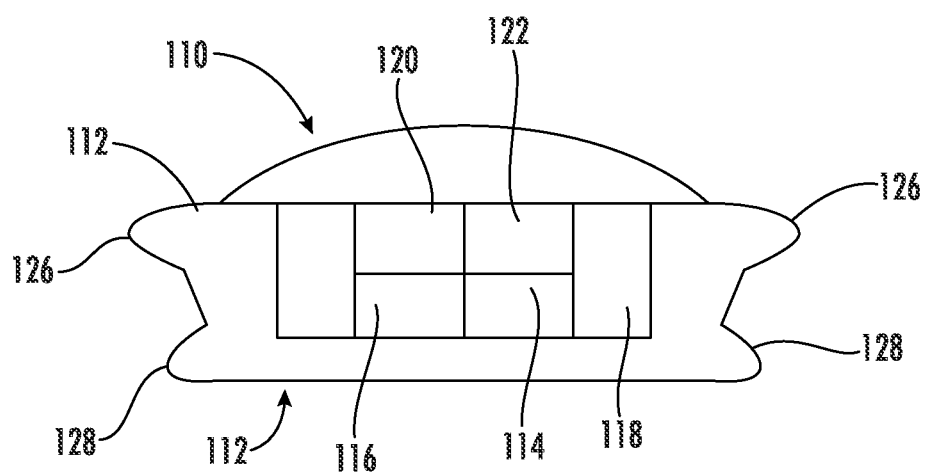
FIG. 5 is a cross-sectional view of the biometric monitoring device of FIG. 4.

With reference now to FIGS. 4 and 5, in at least one embodiment, the housing has a generally disk-like shape, and all of the electronic components of the biometric monitoring device 110 are enclosed within the housing. As shown in FIG. 4, the front of the housing 112 has a generally oval or circular shape such that the housing 112 is void of sharp edges. The front housing further includes a tab 194 that projects outwardly from a top edge of the circular perimeter of the housing. When the biometric monitoring device 110 is mounted in the receptacle 192, the tab 194 is configured to extend past the perimeter of the receptacle 192 in order to allow a finger of the user to quickly engage the tab 194 and dislodge the biometric monitoring device 110 from the receptacle 192.

With particular reference to FIG. 5, the housing 112 includes a sidewall 124 that defines a forward lip 126 and a rearward lip 128. The lips 126, 128 facilitate mounting of the biometric monitoring device 110 within the receptacle 192. For example, the rearward lip 128 may be retained within a groove in the receptacle 192, and the forward lip 126 may cover a rim of the receptacle. An interior chamber is defined within the sidewall and the electronic components of the biometric monitoring device are arranged within the interior chamber. The electronic components including the processor 114, the memory 116, the transceiver 118, the microphone 120, and the speaker are shown side-by-side in FIG. 5, but it will be recognized that the electronic components may be arranged in various forms, such as provided on a circuit board and/or with at least some of the electronic components embedded in epoxy.

With reference again to FIG. 4, the front of the housing 112 also includes a plurality of vent openings 196 that allow for air to pass in and out of the interior of the housing 112. The microphone 120 and the speaker 122 of the biometric monitoring device 110 are oriented to face the vent openings 196, thus facilitating transmission of sound waves into and out of the housing 112.

Two electrical connectors 198 are provided at a bottom portion of the housing 112. The electrical connectors 198 are connected to the electrical components on the interior of the housing 112, extend through the sidewall of the housing 112, and project outwardly from the housing. When the biometric monitoring device 110 is inserted into the receptacle 192, the electrical connectors 198 engage contacts (not shown) in the receptacle that lead to one of the sensor devices. For example, the contacts may lead to electrodes provided as part of a heart rate monitor 140 that is incorporated into the article of apparel 102. In at least one embodiment, the contacts lead to other sensors provided on the article of apparel, such as a respiratory sensor.

With reference again to FIG. 2, the biometric monitoring device 110 is configured to communicate with other devices of the fitness tracking system 100. For example, the biometric monitoring device 110 is configured to communicate with both the personal electronic device 150 and the plurality of sensors 130. In at least one embodiment, the personal electronic device 150 is a smartphone configured to wirelessly communicate with the biometric monitoring device 110 when the two devices are within range of one another, or are both connected to the same wireless network.

The personal electronic device 150 includes a processor 154, a memory 156, a transceiver 158, and an input/output interface 160. The processor 154 is connected to the I/O interface 160, the memory 156, and the transmitter/receiver 158, and is configured to deliver data to and/or receive data from each of these components. The memory 156 is configured to store information, including both data and instructions. The data may be, for example, physiological data as discussed above, which may be related to the activities, workouts, health and fitness profile, etc. of the user, along with other operational data that may be ancillary to the basic operation of the personal electronic device 150. The instructions which are stored at the memory 156 generally include firmware, an operating system, and/or other software for execution by the processor 154. For example, as described in further detail below, the memory 156 of the personal electronic device 150 may include a plurality of exercise modules for use in association with a fitness tracking application. The transceiver 158 of the personal electronic device 150 is configured to transmit and receive communications signals using a wireless communications technology, such as Wi-Fi or Bluetooth®, using any of various communications protocols, such as TCP/IP. The transceiver 158 is particularly configured to communicate with both the biometric monitoring device 110 (e.g., via a local area network) and the remote server 170 (e.g., via a wireless telephone network and/or the Internet 172). The I/O interface may be any of various interfaces commonly used with personal electronic devices, and particularly touchscreens that allow the user to provide input and view output from the personal electronic device 150.

In addition to communications with the personal electronic device 150, the biometric monitoring device 110 is also configured to communicate with the sensors 130, as shown in FIG. 2. The sensors 130 include any number of known sensors configured to collect physiological data (which may also be referred to herein as "workout data" or "sensor data") from the user, such as accelerometers, gyroscopes, magnetometers, electrodes/electrocardiography (ECG) sensors, plethysmography sensors, optical/photoplethysmography (PPG) sensors, or any of various other sensors known in the biometric arts. ECG and PPG sensors are configured to detect heart rate. Accelerometers are configured to detect movement of the user. Gyroscopes are configured to detect orientation and angular velocity of the user. Magnetometers are configured to detect orientation of the user relative to an earth magnetic field. In at least some embodiments, the sensors 130 (which may also be referred to herein as "sensor devices") include at least one inertial measurement unit ("IMU") including a combination of an accelerometer, gyroscope, and magnetometer packaged in a single housing. Communication between each of the sensors 130 and the biometric monitoring device 110 may be via direct wired communication or via wireless communication, depending on the location of the sensor relative to biometric monitoring device. For example, communication between the electrodes of a chest heart rate monitor 140 and the biometric monitoring device 110 may be by direct wired communication, and communication between an IMU 134 on a watch and the biometric monitoring device 110 may be by wireless communication via a known short range communications protocol (e.g., Bluetooth®).

In at least one embodiment, the sensors 130 are configured to periodically transmit sensor data to the biometric monitoring device 110. In this embodiment, the biometric monitoring device 110 listens for sensor transmissions, receives transmitted data from the sensors 130, and then saves the transmitted sensor data in memory 116. As explained in further detail below, the various exercise modules may then use data from selected sensors to generate workout metrics for the user. In yet another embodiment, the sensors 130 are configured to only transmit sensor data to the biometric monitoring device 110 upon receipt of an instruction from the biometric monitoring device 110 to transmit data. In this embodiment, the biometric monitoring device 110 only requests data transmission from particular sensors based on the data requested by a particular exercise module. Data generated by other sensors that are not relevant to the exercise module is ignored, as no transmission request is sent to these sensors.

Figure 6:
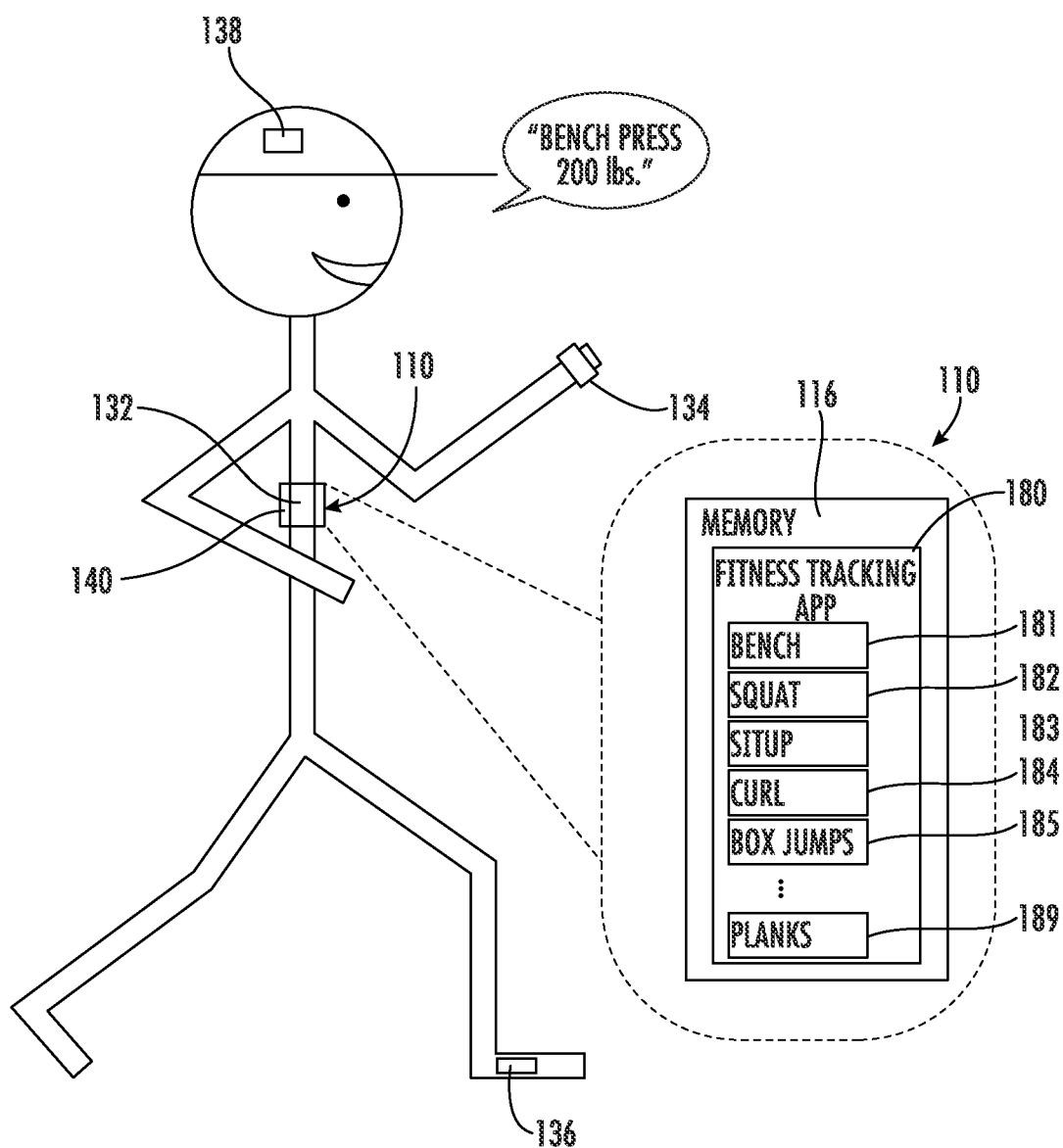
FIG. 6 is an illustration showing sensor locations and various exercise modules retained in a memory of the fitness tracking system of FIG. 1.

The sensors 130 may be mounted on various locations on the body of the user. As shown in the example of FIG. 6, the sensors include the following: (i) a first IMU 132 mounted on an article of apparel 102 along with electrodes for a heart rate monitor 140 in proximity of a user's chest, (ii) a second IMU 134 included on a watch worn on the user's wrist, (iii) a third IMU included on one or more shoes 136 worn on the user's foot, and (iv) a fourth IMU 138 mounted on a hat or other headgear worn on the user's head. Although IMUs 132, 134, 136 and 138 have been used as the example sensor units mounted on the user's chest, wrist, foot and head, in other embodiments, different types of sensors may be used, such as only one of an accelerometer, magnetometer, gyroscope, electrode or other sensor at each of the defined locations. Moreover, while specific mounting locations for the wearable sensors 130 have been defined in the example of FIG. 6, it will be recognized that the sensors may be mounted at numerous other locations on the body of the user, such as the user's waist, leg, arm, back, neck, etc. Also, while each of the sensors 130 may be associated with an article of apparel worn by the user (e.g., a shirt, a shoe, a watch or a hat), in at least some embodiments the one or more sensors may not be associated with an article of apparel and may instead be mounted directly on the skin of the user (e.g., using an adhesive pad to secure the sensor to the skin).

Biometric Monitoring Device with Multiple Exercise Modules

With continued reference to FIG. 6, the memory 116 of the biometric monitoring device 110 includes a fitness tracking app 180 configured to selectively run a plurality of exercise modules. As noted previously, each of these exercise modules is configured to track workout metrics for a user when executing a particular exercise routine. For example, the fitness tracking app 180 may include a bench press module 181, a squat module 182, a sit-up module 183, a curl module 184, a box jump module 185, a plank module 189, and any number of additional exercise modules. Each exercise module is configured to begin execution prior to a user performing the associated exercise and end execution after the user performs the associated exercise. Each exercise module is further configure to receive specific physiological data (i.e., request and/or accept specific data) from at least a first of the wearable sensors 130 during performance of an associated exercise event. At the same time, each exercise module is configured to ignore other physiological data (i.e., do not request or disregard other data) from at least a second of the wearable sensors 130. The exercise module then generates workout metrics for the user based on the input received from the first wearable sensor(s) but without regard to the second wearable sensor(s). The workout metrics generated may be any of various workout metrics, such as repetitions, power output, movement efficiency, energy expenditure, or any of various other workout metrics.

A first example of an exercise module is the bench press module 181. The bench press module 181 may be configured to receive input from a chest-mounted magnetometer, a wrist-mounted accelerometer, and a heart rate sensor. At the same time, the bench press module may be configured to ignore input from a wrist-mounted gyroscope and a foot-mounted accelerometer. The input from the chest-mounted magnetometer allows the module 181 to determine that the user is lying in a supine position, as is common with bench press. The input from the wrist-mounted accelerometer allows the module to determine workout metrics, and specifically repetitions performed with the bench press bar. The input from the heart rate monitor may be used by the module, along with user profile data and other sensor inputs, to calculate calories burned during the exercise. At the same time, other inputs are ignored by the bench press module 181. The input from the wrist-mounted gyroscope may be ignored based on a predetermination that angular velocity measurements on the wrist are not useful for determining bench press metrics. Similarly, the input from the foot-mounted accelerometer is ignored because foot movement is not relevant to the bench press exercise.

A second example of an exercise module is the box jump module 185. The box jump module 185 may be configured to receive input from a chest-mounted magnetometer, foot-mounted gyroscope, and a foot-mounted accelerometer, but may be configured to ignore input from a wrist-mounted gyroscope and wrist-mounted accelerometer. The inputs from the chest mounted magnetometer indicate that the user is upright while the inputs from the foot-mounted gyroscope and accelerometer indicate that the user is performing forward and rearward jumping movements with his or her legs, as is necessary with box jumps. The inputs from the wrist-mounted accelerometer and gyroscope are ignored because these inputs have been determined unreliable or unnecessary data for determining box jump metrics. Based on the received inputs, and other information such as user profile data, various workout metrics are calculated by the box jump module, including number of repetitions and calories burned during performance of the exercise.

The foregoing examples of the bench press module 181 and the box jump module 185 illustrate that each of the exercise modules makes use of different sensor inputs and ignores other sensor inputs. It will be recognized that these modules 181 and 185 may be alternatively configured to receive or ignore different inputs, which inputs are predetermined and programmed to be received by the respective exercise modules. In addition to the modules 181 and 185 discussed above, each of the other modules (e.g., the squat module 182, the sit-up module 183, the curl module, 184, the plank module 189, and any number of additional modules) are also configured to receive inputs from certain sensors and ignore input from other sensors in order to generate workout metrics associated with a particular exercise event.

Because the various exercise modules are configured to receive workout data from two different sensor devices, the fitness tracking system 100 is configured to advantageously detect additional workout data that would not otherwise be detectable. For example, the fitness tracking system 100 is configured to detect repetitions performed by different limbs of the user. Consider a user who is performing dumbbell curls wearing a watch with an accelerometer on a left wrist, and a chest strap with an accelerometer on the torso. The accelerometer on the left wrist will easily detect a repetition of a curl using the left arm. Unfortunately, the accelerometer on the left wrist will not detect repetition of a curl using the right arm. However, the accelerometer on the chest will likely provide the same signal regardless of whether a curl is performed using the left arm or the right arm. Thus, the curl module 184 may be configured to note the chest accelerometer output when a left arm curl is detected based on the left wrist accelerometer output. The curl module then looks for a similar chest accelerometer output when no left arm curl is detected, and recognize that this chest accelerometer output is a right arm repetition. As a result, the curl module 184 is configured to generate improved workout metrics for dumbbell curls performed by the user, including better tracking of repetitions.

While a few exercise modules have been described herein in association with gym-based workouts, it will be recognized that numerous other exercise modules are contemplated herein. In at least one embodiment, the fitness tracking system 100 includes numerous exercise modules that are associated with training drills for particular sports such as football, basketball, volleyball, tennis, etc. For example, consider a tennis player who trains for an hour by volleying, hitting serves, performing footwork drills, and returning serves. The fitness tracking system 100 may include an exercise module associated with each of these events, thus allowing the player to keep track of various workout metrics, such as number of volleys, number of serves hit, number of serves returned, and total calories burned. Thus, the exercise modules described herein are configured to keep track of any number of different workout metrics for any number of different sports.

Voice Activation of Exercise Modules

The biometric monitoring device 110 is configured to execute the fitness tracking app 180 continuously as the user performs a workout consisting of many different exercises (e.g., bench press, sit-ups, squats, lunges, curls, planks, box jumps, etc.). The fitness tracking app 180 may be configured to start and end based on inputs from the user. For example, a switch may be provided on the housing of 112 of the biometric monitoring device 110 that starts and stops execution of the fitness tracking app. In another embodiment, the fitness tracking app 180 begins when the biometric monitoring device 110 is inserted into the receptacle 192 on the article of apparel 102, and ends when the device 110 is removed. In yet another embodiment, the fitness tracking app is executed based on the user starting and ending the app from his or her personal electronic device 150. In any event, the fitness tracking app 180 is configured for use in association with the exercise modules. In particular, specific user input will cause the fitness tracking app to call one of the exercise modules for execution by the processor 114 of the biometric monitoring device 110.

The user input that results in execution of one of the exercise modules may be different in different embodiments of the fitness tracking system 100. In at least one embodiment, the user input is a predetermined prompt followed by voice input or other verbal cue from the user. The predetermined prompt turns on the microphone 120 to allow the user to provide the voice input. In at least one embodiment, the predetermined prompt is a user tap exceeding a threshold force on the housing of the biometric monitoring device 110 (i.e., a "tap-to-talk" prompt). An accelerometer in the housing 112 of the biometric monitoring device 110 provides a signal to the processor 114 indicating that the user has tapped the housing 112, and the processor 114 then turns on the microphone 120 and listens for the voice input from the user. In another embodiment, the microphone is always on when the fitness tracking app 180 is running, and the predetermined prompt itself is a voice input (e.g., "Hey Ski . . . ," "Alexa . . . ," or some other voice prompt). In any event, when the prompt is received, the fitness tracking app 180 immediately listens for a voice input provided by the user at the microphone. The voice input indicates an exercise the user intends to perform next during his or her workout routine. Based on this voice input, the fitness tracking app 180 is configured to select one of the exercise modules that should executed at that time. For example, when the user provides the voice input "Bench Press," the processor 114 selects the bench press module 181 for execution. As another example, when the user provides the voice input "Box Jump," the processor 114 selects the box jump module 185 for execution.

After receiving a voice input from the user, the biometric monitoring device 110 selects one of the appropriate exercise modules for execution by the processor 114. When one of the exercise modules is selected for execution, the transceiver 118 (i) listens for input from the sensor device(s) 130 associated with the selected exercise module and, if appropriate, (ii) sends instructions to the associated sensor device(s) to begin transmission of sensor data.

As the user performs an exercise, physiological data from the sensors 130 is received at the biometric monitoring device and delivered to the processor for use during execution of the exercise module. As noted previously, each exercise module receives workout data from specific sensors and ignores workout data from other sensors. Additionally, each exercise module looks for certain data markers that are known to be associated with the exercise being performed by the user. For example, the bench press module may look for both (i) a first data marker from the chest-mounted gyroscope indicative of the user in a supine position, and (ii) a second data marker from the from the wrist-mounted accelerometer that the user's arm has moved forward (e.g., outward movement from the chest) and then expectedly stopped after some distance of travel (e.g., when the user's arms are fully extended), thus indicative of a bench press repetition.

In at least one embodiment, the voice input provided by the user indicates not only (i) an exercise module to be executed, but also (ii) specific parameters to be used in during execution of the exercise module in order to arrive at more detailed workout metrics. For example, if the user provides a voice input of "squat 300 pounds," the squat module 182 will be executed and the workout metrics calculated will based at least in part on the provided weight parameter of 300 pounds. By providing this additional weight data, even more accurate workout metrics are calculated. To illustrate this, consider a user who performs a number of squats using only a 45 pound bar on a light workout day, but performs the same number of squats with three hundred pounds of weight on a heavy workout day. Without the additional weight parameter provided to the squat module 182, the module will generate the same workout metrics for both the light workout day and the heavy workout day, although the user clearly burned more calories from squats on the heavy workout day.

Termination Events

Preferably, each exercise module is only executed for a limited period of time associated with performance of the associated exercise by the user. Therefore, each exercise module is associated with and configured to detect termination events indicative of the user ending the exercise. Execution of the exercise module terminates upon detection of these termination events.

The termination events are provided by workout data from the sensors. For example, if the input from the chest-mounted magnetometer indicates that the user has moved from a supine position to an upright position, this may be considered a termination event indicative of the user ending the exercise. Similarly, if too much time passes between repetitions (i.e., a predetermined period of time such as ten seconds passes before receipt of a subsequent data marker indicative of another bench press repetition), this may be considered a termination event indicative of the user ending the exercise. Termination events may also occur before the user performs any exercise repetitions. For example, if the chest-mounted magnetometer indicates that the user has not moved into a supine position within thirty seconds after the start of the bench press module, or if the wrist-mounted accelerometer indicates that no repetitions have occurred within thirty seconds after the start of the bench press module, a termination event may be determined. When a termination event is detected, execution of the exercise module ends.

In at least one embodiment, each exercise module receives input from one sensor for the primary purpose of determining that a termination event has occurred (i.e., not for the purpose of obtaining workout data). Many exercises are performed in a relatively stationary position. With these exercises, determining that the user is walking suggests that the user has terminated the exercise (e.g., a user who is walking is not performing a bench press). Therefore, sensor data indicating that the user is walking may be a termination event for certain exercise modules. For example, each of the bench press module 181, squat module 182, sit-up module 183, curl module 184, and plank module 189 may be configured to receive input from the foot accelerometer sensor for the primary purpose of determining a termination event associated with the user is walking. When the data from the foot accelerometer sensor shows that the user is walking, a termination event occurs, and the module ends execution.

In at least one embodiment, termination events may be gestures provided by the user to indicate that an exercise has ended. For example, a gesture may be a hand wave, fist pump, finger snap, clap, jump or any of various other gestures that may be used as termination events. In each embodiment, one of the sensors is configured to generate a signal that recognizes the gesture and is indicative of a termination event. In some embodiments, the user may self-select gestures to use as a termination event, and the appropriate signal associated with the gesture is trained through a gesture recognition algorithm. As a result a gesture indicative of a termination event may be quickly recognized by system. For example, the user may place one or more sensors in a gesture recognition mode and repeatedly perform the desired gesture (e.g., a hand wave, a fist pump, jump, etc.) until the sensor and system is sufficiently trained to recognize the gesture. The gestured trained into the system using the gesture recognition algorithm may be selected by the user from a predetermined list of available gestures or may be created by individual users. For example, if a user decides that his or her unique gesture indicative of a termination event should be a combination of a clap and a snap, the user may train this combination to be the gesture indicative of a termination event.

Voice Logging of RPE

In at least one embodiment, the fitness tracking system 100 is further configured to receive a voice input providing a record of perceived exertion (RPE). The RPE is typically provided as a number from one to ten that indicates the level of difficulty associated with performance of the exercise. A one is a very easy exercise, and a ten is a very difficult exercise for the user.

In at least one embodiment the microphone 120 listens for an RPE voice input from the user for a limited period of time following a termination event. Alternatively, the microphone 120 listens for an RPE voice input during execution of the exercise module and receipt of the RPE voice input is used as the termination event for the exercise module. The voice input of the RPE may be provided in a predetermined format with a keyword to indicate that the user is providing a RPE voice input. For example, the term "RPE" may provide the keyword when the user says "RPE seven." As another example, the phrase "That was a . . . " may provide the keyword indicating an RPE will follow when the user says "That was a seven."

When an RPE is received, the RPE is associated with the recently completed workout data and/or workout metrics in the memory 116. For example, when a user completes a set of 200 lb. bench presses and says "RPE seven," an RPE of seven is stored in a database in the memory 116 in association with the other workout data, such as the workout performed, number of repetitions, weight used, etc. In at least one embodiment, the RPE may be used by the fitness tracking app to provide recommendations/coaching to the user in association with future workouts. These recommendations may be based on the user's predefined goals, personal demographics (e.g., age, etc.), or any of various other factors. For example, if a user consistently provides an RPE input of four or five in association with a bench press exercise, and a user goal is to increase strength, the fitness tracking system 100 may provide feedback via the user's personal electronic device encouraging the user to slightly increase the weight when performing future sets of the bench press. As another example, if the user consistently provides an RPE input of nine or ten in association with another exercise, the fitness tracking system 100 may recognize that the user is risking injury and encourage the user to reduce the weight associated with the exercise or decrease the number of repetitions. In this manner, the fitness tracking system may assist the user in avoiding injury while still achieving his or her personal fitness goals.

Machine Learning with Exercise Modules

In at least one alternative embodiment, the fitness tracking system 100 uses machine learning to determine which sensor inputs should be associated with a particular exercise module for the user, and which sensor inputs should be ignored for such exercise module. Each exercise module typically includes two or three predetermined sensor inputs that are received and used to calculate workout metrics. However, over time, the fitness tracking system 100 may determine that one or more additional or different sensor inputs also provide useful workout data for a particular user performing a particular workout. This may be true even though the same workout data would be useless for another user. For example, consider a particular user who repeatedly performs a bench press routine with his or her legs in a raised position (e.g., in a feet and ankles crossed position or in a standard leg-raise position) as opposed to the more common position of feet on the floor. This user may tend to kick or move his or her feet with each bench press repetition. Over time, the fitness tracking system may recognize that the workout data from the shoe-mounted sensor is correlated with the standard bench press repetition data typically provided by a wrist-mounted sensor 134. When this correlation is made, the fitness tracking app 180 may then begin to look for input from either or both of the wrist-mounted sensor 134 and the shoe mounted sensor 136 in order to determine bench press repetitions when executing the bench press module 181. Advantageously, if the user's wrist-mounted sensor 134 is unavailable (e.g., the user is not wearing the smart watch or the watch is out of power), the bench press module 181 may simply obtain repetition data from the shoe sensor, and vice-versa. Thus, it will be recognized that the fitness tracking system is equipped with the ability to dynamically adjust the different sensors that are recognized or ignored in association with each of the workout modules.

The machine learning may also determine whether a predetermined exercise definition associated with a particular workout module should be amended based on the user's workout performances. Each exercise module may include a number of predetermined conditions that the fitness tracking app 180 monitors as indicative of the user performing the exercise. For example, as noted previously, the bench press module 181 may look for input from the user's chest-mounted sensor 132 indicating that the user is in a supine position. However, consider a user who repeatedly performs an incline press (e.g., heads-up/head of bed 30°) each time the user provides the voice input of "bench press." The fitness tracking system 100 may be configured to use machine learning to determine that a "bench press" voice input from this user is not limited to a sensor input indicative of the supine position, but may also be associated with sensor input indicative of an inclined, heads-up position. Alternatively, the fitness tracking system 100 may be configured to use machine learning to determine that the user is actually performing an incline press instead of a bench press, and use a different module to determine workout metrics, notwithstanding the fact that the user provided the "bench press" voice input.

In addition to the foregoing, machine learning may advantageously be used to make exercise module selections for the user even if the user fails to provide a voice input. In this embodiment, the system looks for specific initiation events indicative of the user beginning a particular exercise. The initiation events may include any number of different inputs, such as user orientation, input from specific sensors, and specific signal patterns from such signals indicative of the user performing a particular exercise. For example, even if the user fails to provide the "bench press" voice input, the fitness tracking app 180 may monitor all sensor inputs, recognize that the user is in a supine position, and recognize that the signals from the sensors are of the same pattern as commonly provided when the user performs a bench press. The sensor inputs may include all of the sensor inputs, including those that are typically ignored for the purpose of generating workout data. In this manner, if the combination of inputs from the wrist-mounted sensor 134 and the foot sensor 136 are indicative of the user preforming a bench press, the fitness tracking app 180 may begin counting repetitions for bench press even though no voice input has been provided from the user. While the wrist-mounted sensor 134 may be the sensor that determinatively indicates that a repetition has occurred for purposes of generating workout metrics, but the foot mounted sensor is nevertheless used for determining that the user is actually performing a bench press routine. Thus, although the foot mounted sensor may be considered to be "ignored" for the purpose of generating workout metrics (i.e., it is not used to generate actual bench press metrics), it may at the same time be received and used for the purpose of determining that the user is actually performing a workout routine (e.g., the bench press).

In the above-described embodiment with machine learning capability, the machine learning typically occurs at the remote server 170 (see FIG. 1) using workout metrics that have been transmitted from the biometric monitoring device 110 and the personal electronic device 150 over many workouts that occurred over many days. The remote server 170 updates the fitness tracking app 180 for the user, including various updated exercise modules, and transmits the updated fitness tracking app 180 to the personal electronic device 150. When the biometric monitoring device 110 is moved into range of the personal electronic device 150, the biometric monitoring device is updated to include the most recent version of the fitness tracking app 180 for the individual user.

Method of Operating a Fitness Tracking System

Figure 7:
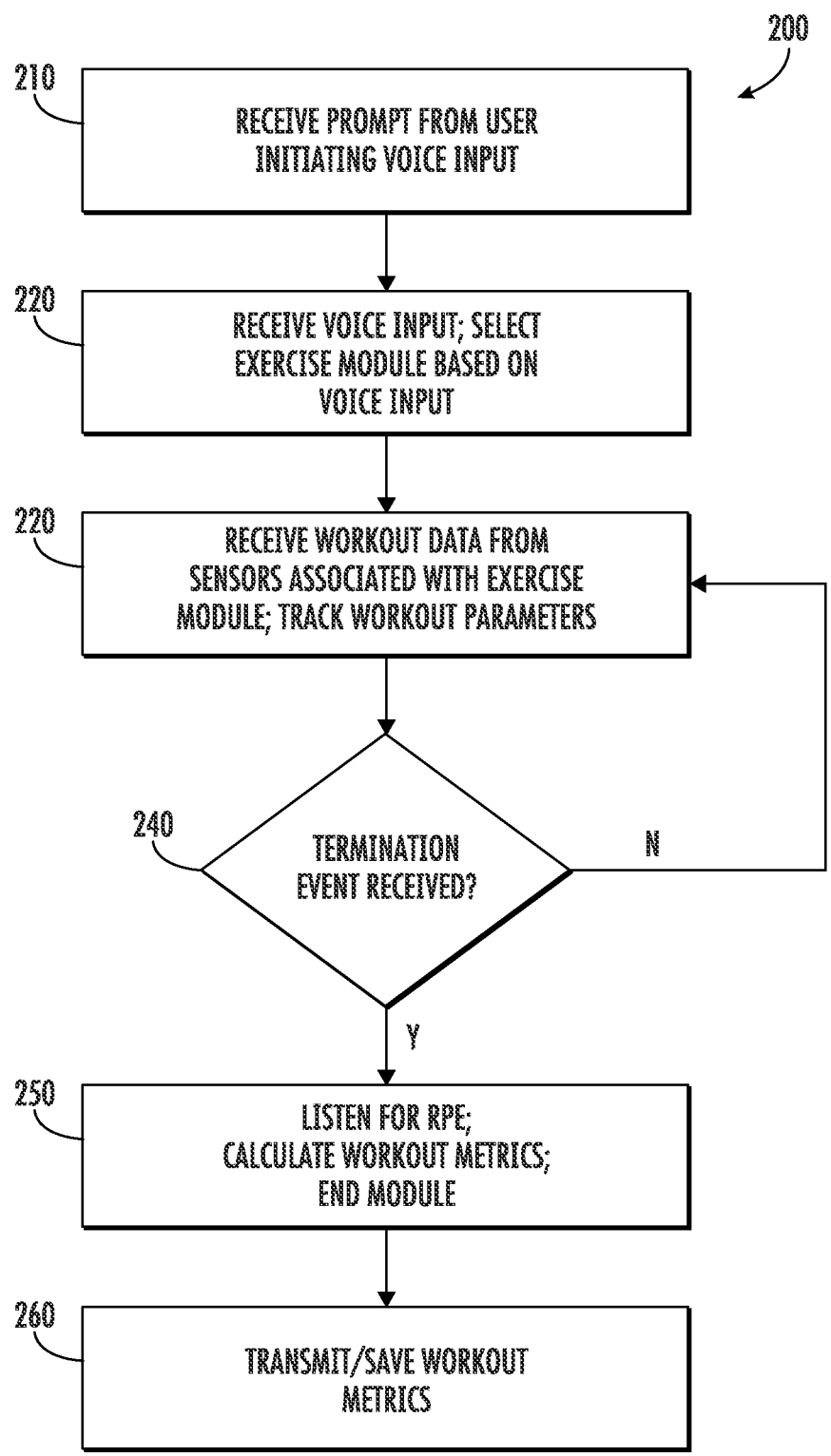
FIG. 7 is a flowchart of a method of determining workout metrics using the fitness tracking system of FIG. 1.

With reference now to FIG. 7 a block diagram of a method of operating a fitness tracking system 100 is shown. The method is performed in association with a fitness tracking system 100 that includes a biometric monitoring device 110 mounted on an article of apparel worn by a user (e.g., on a shirt, chest strap, etc.). The method begins at block 210 when the biometric monitoring device 110 receives a prompt from the user indicating that he or she is about to provide a voice input indicating selection of an exercise module. As noted above, the prompt may be provided in any of various forms, such as a tap-to-talk or receipt of a keyword.

After receiving the prompt from the user at block 210, the method moves to block 220. At block 220, the fitness tracking app 180 listens for a voice input from the user via the microphone 120 of the biometric monitoring device 110. Based on the voice input received from the user, the fitness tracking app 180 selects one of the plurality of exercise modules to execute. For example, if the user provides a voice input of "squat 200 lbs.," the fitness tracking app selects the squat module 182 for execution.

With the appropriate exercise module selected, the method moves on to block 230, and receives workout data from the sensor devices 130 associated with the selected exercise app. As discussed previously, each of the exercise modules receives and accepts input from certain sensor devices 130, but ignores input from other sensor devices. Based on the workout data received, the exercise module is able to track various workout parameters, such as the number of repetitions performed for a particular exercise (e.g., 12 squats).

As the fitness tracking app 180 receives workout data from the sensors, it also monitors for termination events as noted in block 240. Termination events indicate that the user has stopped the exercise and is about to move on to something else. For example, as discussed previously, if the sensors indicate that the user is walking during execution of the bench press module, this may be a termination event indicating that the user has completed the bench press exercise. Other termination events are also contemplated, such as the passing of a predetermined period of time since the occurrence of the last repetition of the exercise. As noted in block 240, if no termination event is received, the method returns to block 230 and continues to receive workout data from the sensors associated with the exercise module. However, when a termination event is received at block 240, the method moves on to block 250.

At block 250, the method continues by listening for voice input of an RPE from the user and calculating workout metrics. The workout metrics include specific data associated with performance of the exercise, such as total number of repetitions, calories burned, time required to perform the exercise, etc. If an RPE is received, the RPE is associated with the workout metrics. Once all of the workout metrics are completed and an RPE is received (if any), the exercise module ends. Then, in block 260, the method continues by transmitting the calculated workout metrics and RPE (if any) to the personal electronic device 150 of the user. If the personal electronic device 150 is not in range for data transmission between the devices, the workout metrics and RPE are saved in the memory of the biometric monitoring device until the personal electronic device 150 is moved within range.

In view of all of the foregoing, it will be recognized that the herein described applications (e.g., fitness tracking application 180 and the various exercise modules) improve the functioning of a fitness tracking system 100 that includes a plurality of wearable sensor devices, a biometric monitoring device, and a personal electronic device, respectively, or in combination. The improved fitness tracking system is configured to generate biometric data during a user workout in a manner that was not previously possible. The fitness tracking system 100 is particularly useful in association with workouts wherein a plurality of different exercises are performed by the user during the workout. One example of such a workout is a gym workouts wherein the user performs exercises in many different positions using many different weight combinations. Another example of such a workout is a sport-specific workout where the user performs specific drills related to a specific sport (e.g., football, basketball, tennis, etc.). As explained previously, such workouts are typically characterized by inter-individual variations as well as intra-individual variations that make the generation of biometric data in association with such workouts extremely difficult. The fitness tracking system 100 described herein addresses these inter- and intra-individual variations and makes accurate tracking of biometric data from such workouts automatic and much more convenient for the user.

The foregoing detailed description of one or more exemplary embodiments of the fitness tracking system has been presented herein by way of example only and not limitation. It will be recognized that there are advantages to certain individual features and functions described herein that may be obtained without incorporating other features and functions described herein. Moreover, it will be recognized that various alternatives, modifications, variations, or improvements of the above-disclosed exemplary embodiments and other features and functions, or alternatives thereof, may be desirably combined into many other different embodiments, systems or applications. Presently unforeseen or unanticipated alternatives, modifications, variations, or improvements therein may be subsequently made by those skilled in the art which are also intended to be encompassed by the appended claims. Therefore, the spirit and scope of any appended claims should not be limited to the description of the exemplary embodiments contained herein.

It will be appreciated that the various ones of the foregoing aspects of the present disclosure, or any parts or functions thereof, may be implemented using hardware, software, firmware, tangible, and non-transitory computer readable or computer usable storage media having instructions stored thereon, or a combination thereof, and may be implemented in one or more computer systems.

What is claimed is:

1. A fitness tracking system comprising:
an article of apparel configured to encircle a torso of a user, the article of apparel including a receptacle;
a plurality of sensors worn by the user, each of the plurality of sensors configured to generate physiological data for the user;
a biometric monitoring device releasably mounted in the receptacle of the article of apparel, the biometric monitoring device including a processor, a memory, a transceiver, at least one microphone, and at least one sensor of the plurality of sensors, the processor being configured to:
receive a prompt indicating that the user intends to provide a verbal cue via the at least one microphone;
receive the verbal cue from the user via the at least one microphone;
in response to the received verbal cue, select one of a plurality of exercise modules for execution by the processor, each of the plurality of exercise modules configured to generate workout metrics based at least in part on physiological data received from a first sensor of the plurality of sensors without regard to physiological data from a second sensor of the plurality of sensors, each of the plurality of exercise modules associated with a termination event; and
execute the selected exercise module in order to generate workout metrics for the user, wherein execution of the selected exercise module occurs for a limited period of time ranging from selection of the exercise module until occurrence of the termination event.

2. The system of claim 1 wherein the verbal cue includes both (i) identification of an exercise to be performed, and (ii) identification of a weight associated with the exercise.

3. The system of claim 2 wherein each of the plurality of exercise modules is configured to generate workout metrics based at least in part on user profile data and the identified weight associated with the exercise.

4. The system of claim 1 wherein the prompt indicating that the user intends to provide a verbal exercise selection via the microphone is a signal from an accelerometer indicating that the user tapped a housing of the biometric monitoring device.

5. The system of claim 1 wherein each of the plurality of exercise modules is configured to detect a number of repetitions performed by the user based at least in part on the physiological data from the first sensor.

6. The system of claim 5 wherein the termination event is a predetermined period of time during which no repetitions are performed by the user.

7. The system of claim 1 wherein the termination event is detection of the user walking based on the physiological data from one of the plurality of sensors.

8. The system of claim 7 wherein detection of the user walking is based on the physiological data from the second sensor.

9. The system of claim 1 wherein the workout metrics include one or more of the following metrics: repetitions, power output, movement efficiency, and energy expenditure.

10. The system of claim 1 wherein the processor is further configured to receive a verbal input of rated perceived exertion (RPE) from the user via the at least one microphone, wherein the verbal input of the RPE provides the termination event.

11. The system of claim 1 wherein the biometric monitoring device includes a plurality of microphones.

12. The system of claim 1 wherein the biometric monitoring device is further configured to transmit the workout metrics to a personal electronic device at a time after the termination of the workout event.

13. The system of claim 12 wherein the personal electronic device is further configured to transmit the workout metrics to a remote server, wherein the remote server is configured to update the selected exercise module such that the exercise module is configured to generate workout metrics based at least in part on physiological data received from a third sensor of the plurality of sensors without regard to physiological data from the first sensor of the plurality of sensors.

14. The system of claim 1 wherein the processor, the memory, the transceiver, the at least one microphone, and the at least one sensor of the biometric monitoring device are all retained within a housing that is void of a screen.

15. A method of operating a fitness tracking system comprising:
receiving a prompt indicating that a user wearing a biometric monitoring device intends to provide a verbal cue via at least one microphone provided on the biometric monitoring device;
receiving the verbal cue from the user via the at least one microphone;
in response to the received verbal cue, selecting one of a plurality of exercise modules for execution by a processor of the biometric monitoring device, each of the plurality of exercise modules configured to generate workout metrics based at least in part on physiological data received from a first sensor worn by the user and without regard to a second sensor worn by the user, each of the plurality of exercise modules associated with a termination event;
executing the selected exercise module in order to generate workout metrics for the user;
receiving a termination event at the biometric monitoring device; and
terminating execution of the selected exercise module following receipt of the termination event.

16. The method of claim 15 wherein the first sensor for a first of the plurality of exercise modules is a different sensor than the first sensor for a second of the plurality of exercise modules.

17. The method of claim 14 wherein the termination event is one of (i) a signal from at least one third sensor indicative of the user walking, (ii) a voice input from the user indicative of the termination event, or (iii) a signal from at least one sensor indicative of a termination event, the signal trained through a gesture recognition algorithm to recognize a gesture indicative of the termination event.

18. The method of claim 15 wherein each of the plurality of exercise modules is configured to detect a number of repetitions performed by the user based at least in part on the physiological data from the first sensor.

19. A method of operating a fitness tracking system comprising:
receiving, at a biometric monitoring device worn by a user, physiological data from a plurality of sensors worn by a user, each of the plurality of sensors positioned at a different location on a body of the user;
receiving a prompt indicating that the user intends to provide a verbal cue via at least one microphone provided on the biometric monitoring device;
receiving the verbal cue from the user via the at least one microphone;
in response to the received verbal cue, selecting one of a plurality of exercise modules for execution by a processor of the biometric monitoring device;
generating workout metrics for the user using the selected exercise module, the generated workout metrics based at least in part on the physiological data received from one of a plurality of sensors worn by the user and without regard to physiological data received from another of the plurality of sensors worn by the user; and
transmitting the generated workout metrics to a personal electronic device.

20. The method of claim 19 wherein the plurality of exercise modules include a plurality of gym-based exercise modules comprising at least a bench press module, a squat module, and a curl module.

* * * * *